United States Patent
Yoshimoto et al.

(10) Patent No.: US 7,862,747 B2
(45) Date of Patent: Jan. 4, 2011

(54) ARYLSULFONIC ACID COMPOUND AND USE THEREOF AS ELECTRON-ACCEPTOR MATERIAL

(75) Inventors: Takuji Yoshimoto, Funabashi (JP); Go Ono, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 865 days.

(21) Appl. No.: 11/661,280

(22) PCT Filed: Aug. 30, 2005

(86) PCT No.: PCT/JP2005/015689
§ 371 (c)(1),
(2), (4) Date: Feb. 27, 2007

(87) PCT Pub. No.: WO2006/025342
PCT Pub. Date: Mar. 9, 2006

(65) Prior Publication Data
US 2008/0029742 A1  Feb. 7, 2008

(30) Foreign Application Priority Data
Aug. 31, 2004 (JP) .................... 2004-251774

(51) Int. Cl.
H01B 1/00 (2006.01)
H01L 29/08 (2006.01)
H01L 35/24 (2006.01)

(52) U.S. Cl. ........................... 252/500; 257/40
(58) Field of Classification Search ............ 252/500; 257/40
See application file for complete search history.

(56) References Cited

U.S. PATENT DOCUMENTS

| 2,884,446 | A | * | 4/1959 | Sien et al. ............. 562/59 |
| 3,646,005 | A | * | 2/1972 | Roe et al. ............. 562/71 |
| 4,952,235 | A | * | 8/1990 | Andree et al. .......... 504/251 |
| 7,579,427 | B2 | * | 8/2009 | Gao et al. ............. 528/150 |
| 2005/0082514 | A1 | | 4/2005 | Yoshimoto et al. |

FOREIGN PATENT DOCUMENTS

| EP | 1 477 993 A1 | | 11/2004 |
| JP | H09-158091 | * | 6/1997 |
| JP | 2000-204158 A | | 7/2000 |
| JP | 2002-151272 A | | 5/2002 |
| WO | WO-03/071559 A1 | | 8/2003 |

OTHER PUBLICATIONS

Tang et al., Applied Physics Letters, vol. 51, No. 12, Sep. 12, 1987, pp. 913-915.
Burroughes et al., Nature, vol. 347, Oct. 11, 1990, pp. 539-541.
Van Slyke et al., Applied Physics Letters, vol. 69, No. 15, Oct. 7, 1996, pp. 2160-2162.
Gustafsson et al., Nature, vol. 357, Jun. 11, 1992, pp. 477-479.
Yang et al., Applied Physics Letters, vol. 64, No. 10, Mar. 7, 1994, pp. 1245-1247.
Bharathan et al., Applied Physics Letters, vol. 72, No. 21, May 25, 1998, pp. 2660-2662.
Wakimoto et al., IEEE Transactions on Electron Devices, vol. 44, No. 8, Aug. 1997, pp. 1245-1248.
Ganzorig et al., Japanese Journal of Applied Physics, vol. 38, No. 11B, Pt. 2, Nov. 15, 1999, pp. L1348-L1350.
Ochi et al., Bulletin of Chemical Society of Japan, vol. 67, No. 6, Jun. 1994, pp. 1749-1752.
Nakayama et al., Heterocycles, vol. 26, No. 4, Apr. 1, 1987, pp. 939-942.
Nakayama et al., Heterocycles, vol. 26, No. 7, Jul. 1, 1987, pp. 1793-1796.

* cited by examiner

*Primary Examiner*—Mark Kopec
*Assistant Examiner*—Jaison P Thomas
(74) *Attorney, Agent, or Firm*—Birch, Stewart, Kolasch & Birch, LLP

(57) ABSTRACT

An excellent EL device having low driving voltage, high luminous efficiency and long life can be obtained by using a charge-transporting thin film composed of a charge-transporting varnish which contains an arylsulfonic acid compound represented by the formula (1) or (2) below as an electron-acceptor material especially in an OLED device or a PLED device.

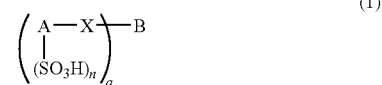

(1)

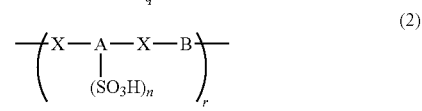

(2)

[In the formulae, X represents O, S or NH; A represents a naphthalene ring or anthracene ring having a substituent other than X and n $SO_3H$ groups; B represents a substituted or unsubstituted hydrocarbon group, 1,3,5-triazine group or a substituted of unsubstituted group represented by the following formula (3) or (4):

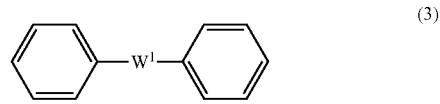

(3)

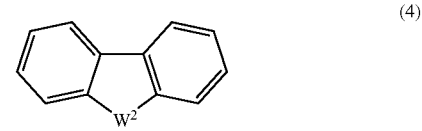

(4)

(wherein $W^1$ and $W^2$ each independently represents O, S, an S(O) group, an $S(O_2)$ group, or a substituted or unsubstituted N, Si, P or P(O) group); n indicates the number of sulfonic acid groups bonded to A which is an integer satisfying $1 \leq n \leq 4$; q indicates the number of B—X bonds which is an integer satisfying $1 \leq q$; and r indicates the number of recurring units which is an integer satisfying $1 \leq r$.].

9 Claims, No Drawings

ARYLSULFONIC ACID COMPOUND AND USE THEREOF AS ELECTRON-ACCEPTOR MATERIAL

TECHNICAL FIELD

This invention relates to an arylsulfonic acid compound, and also to use of this compound as an electron-acceptor material. As this use, a varnish containing an electron-acceptor material including the arylsulfonic acid compound, a charge-transporting thin film formed by using the varnish or an organic electroluminescent (hereinafter abbreviated as "organic EL") device formed by using the charge-transporting thin film, or the like can be mentioned.

BACKGROUND ART

Organic EL devices, especially low-molecular organic EL (hereinafter abbreviated as "OLED") devices were significantly improved in characteristics, such as a substantial reduction in drive voltage, by Eastman Kodak Company owing to the separation of functions as a result of the formation of an organic layer into an ultrathin film and a multilayer construction (Non-patent Document 1: Applied Physics Letters, Vol. 51, pp. 913-915, U.S.A. (1987)).

Further, organic EL (hereinafter abbreviated as "PLED") devices making use of a high-molecular light-emitting material were developed by University of Cambridge (Non-patent Document 2: Nature, Vol. 347, pp. 539-541, Great Britain (1990)). Characteristics of high-molecular organic EL devices in recent years have been improved to such a level as favorably comparable with those of conventional OLED devices.

Concerning the above-described OLED devices, it has been reported that the arrangement of a copper phthalocyanine (CuPC) layer as a hole injection layer can improve initial-stage characteristics, such as a reduction in drive voltage and an improvement in luminescence efficiency, and further can materialize improvements in life characteristics (Non-patent Document 3: Applied Physics Letters, Vol. 69, pp. 2160-2162, U.S.A. (1996)).

With respect to PLED devices, on the other hand, it has been reported that the use of a polyaniline material (Non-patent Document 4: Nature, Vol. 357, pp. 477-479, Great Britain (1992); Applied Physics Letters, Vol. 64, pp. 1245-1247, U.S.A. (1994)) or a polythiophene material (Non-patent Document 5: Applied Physics Letters, Vol. 72, pp. 2660-2662, U.S.A. (1998)) as a hole transport layer (buffer layer) can bring about similar advantageous effects as the OLED devices.

It was also found that the use of a metal oxide (Non-patent Document 6: IEEE Transactions on Electron Devices, Vol. 44, pp. 1245-1248, U.S.A. (1997)), a metal halide (Non-patent Document 7: Applied Physics Letters, Vol. 70, pp. 152-154, U.S.A. (1997)), a metal complex (Non-patent Document 8: Japanese Journal of Applied Physics, Vol. 38, pp. L1348-1350 (1999)) or the like as an electron injection layer leads to improved initial characteristics. These charge injection layers and buffer layers have then found widespread utility.

Recently, a charge-transporting varnish of an organic solvent system, which makes use of a low-molecular oligoaniline material, has been developed, and the insertion of a hole injection layer obtained by using this varnish has been found to show excellent EL device characteristics (Patent Document 1: JP-A 2002-151272).

CuPC, a common hole injection material for OLED devices, however involves a drawback that it tends to result in a film having a very rough surface and its mixing in a trace amount in another organic layer leads to substantially deteriorated characteristics.

Polyaniline materials and polythiophene materials, which are currently employed in PLED devices, involve problems in that they contain as a solvent water having a potential problem of promoting a device deterioration, a limitation is imposed on usable solvents, and due to the aggregation and low solubility of the material, a limitation is also imposed on the coating method capable of forming a uniform film.

The use of a charge-transporting varnish of an organic solvent system, which contains a low-molecular oligoaniline material having high solubility, may also develop problems such that a limitation is imposed on the kind of usable electron-accepting dopants and the electron-accepting dopants are low in heat resistance and amorphousness. A charge-transporting varnish containing a charge-transporting material and charge-accepting dopant material of low molecular weights, especially a varnish containing a crystalline material may generally have a difficulty in forming a film which shows high levelness.

Patent Document 1:
JP-A 2002-151272
Non-patent Document 1:
Applied Physics Letters, Vol. 51, pp. 913-915, U.S.A. (1987)
Non-patent Document 2:
Nature, Vol. 347, pp. 539-541, Great Britain (1990)
Non-patent Document 3:
Applied Physics Letters, Vol. 69, pp. 2160-2162, U.S.A. (1996)
Non-patent Document 4:
Nature, Vol. 357, pp. 477-479, Great Britain (1992)
Non-patent Document 5:
Applied Physics Letters, Vol. 64, pp. 1245-1247, U.S.A. (1994)
Non-patent Document 6:
Applied Physics Letters, Vol. 72, pp. 2660-2662, U.S.A. (1998)
Non-patent Document 7:
IEEE Transactions on Electron Devices, Vol. 44, pp. 1245-1248, U.S.A. (1997)
Non-patent Document 8:
Japanese Journal of Applied Physics, Vol. 38, pp. L1348-1350 (1999)

DISCLOSURE OF INVENTION

Problems to be Solved by the Invention

With the foregoing circumstances in view, the present invention has as an object thereof the provision of an arylsulfonic acid compound suitable as an electron-acceptor material, which can materialize high uniform film-forming property and, especially when applied to OLED devices and PLED devices, can materialize excellent EL device characteristics such as low drive voltage, high luminescence efficiency and long life.

Means for Solving the Problems

The present inventors have proceeded with an extensive investigation to achieve the above-described object. As a result, it has been found that arylsulfonic acid compounds represented by the formula (1) have high heat resistance, show amorphousness, and moreover, are materials soluble in organic solvents such as N,N-dimethylformamide (hereinafter abbreviated as "DMF"); and also that, when these arylsulfonic acid compounds are combined with charge-transporting host materials, the compounds accept electrons from the charge-transporting host substances to improve the charge transport ability and, when used as hole injection layers in OLED devices and the like, the compounds make it possible to further improve the low-voltage drive and luminescence efficiency.

It has also been found that, when these compounds are used even in combination with crystalline charge-transporting host materials, the resulting charge-transporting thin films show high amorphousness.

The present invention, therefore, provides the following aspects [1] to [5]:

[1] An arylsulfonic acid compound represented by the following formula (1) or (2):

[Chemical Formula 1]

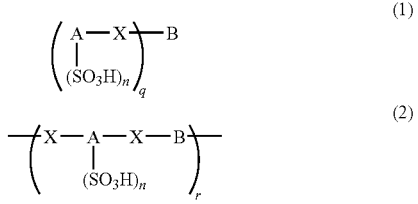

wherein

X represents O, S or NH,

A represents a naphthalene or anthracene ring which may contain one or more substituents other than X and $(SO_3H)n$, B represents an unsubstituted or substituted hydrocarbon group, a 1,3,5-triazine group, or an unsubstituted or substituted group represented by the following formula (3) or (4);

[Chemical Formula 2]

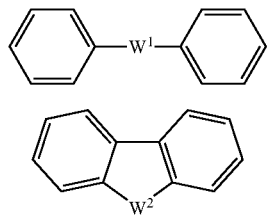

wherein $W^1$ and $W^2$ each independently represents O, S, an S(O) group, an $S(O_2)$ group, or an unsubstituted or substituted N, Si, P or P(O) group, n indicates a number of sulfonic acid group(s) bonded to A, and stands for an integer satisfying $1 \leq n \leq 4$, q indicates a number of B—X bond(s), and stands for an integer satisfying $1 \leq q$, and r indicates a number of recurring unit(s), and stands for an integer satisfying $1 \leq r$.

[2] An arylsulfonic acid compound as described above under [1], wherein B is a divalent or trivalent, substituted or unsubstituted benzyl group, a divalent, substituted or unsubstituted p-xylylene group, a divalent or trivalent, substituted or unsubstituted naphthyl group, a divalent or trivalent-1,3,5-triazine group, a divalent, substituted or unsubstituted diphenylsulfone group, a di- to tetra-valent, perfluorobiphenyl group, a divalent, substituted or unsubstituted 2,2-bis((hydroxypropoxy)phenyl)propyl group, or a substituted or unsubstituted polyvinylbenzyl group.

[3] An electron-acceptor material comprising an arylsulfonic acid compound as described above under [1] and [2].

[4] A charge-transporting varnish comprising an electron-acceptor material as described above under [3], a charge-transporting material, and a solvent.

[5] A charge-transporting thin film comprising an electron-acceptor material as described above under [3] and a charge-transporting material.

[6] An organic electroluminescent device comprising a charge-transporting thin film as described above under [5].

EFFECTS OF THE INVENTION

The arylsulfonic acid compound of the invention not only shows amorphous solidity at room temperature but also has high solubility in various organic solvents. Accordingly, use of a charge-transporting varnish of an organic solvent system, which contains the above compound as a dopant, makes it possible to readily form an amorphous solid thin film.

Further, use of a thin film, which has been formed with the arylsulfonic acid compound of the invention contained therein, as a hole injection layer or hole transport layer makes it possible to lower the drive voltage for an organic EL device, to improve the current efficiency of light emission, and also to obtain a uniform light-emitting surface.

Different from the charge-transporting varnishes of aqueous solution systems which have been used conventionally, the arylsulfonic acid compound of the invention can be used with an organic solvent alone, thereby making it possible to avoid any deterioration of an EL device which would otherwise take place by penetration of water into the device.

The charge-transporting varnish of the organic solvent system, which contains the arylsulfonic acid compound of the invention as an electron-accepting dopant material, can be applied for capacitor-electrode protecting films, antistatic films, ion conductor films, solar batteries, fuel cells and the like.

BEST MODES FOR CARRYING OUT THE INVENTION

The present invention will hereinafter be described in further detail.

In the arylsulfonic acid compound represented by the formula (1) or (2), A represents a naphthalene or anthracene ring which may contain substituents other than X and $(SO_3H)_n$.

Specific examples of the substituents other than X and $(SO_3H)$ include, but are not limited to, hydroxyl, amino, silanol, thiol, carboxyl, sulfonic acid, phosphoric acid, phosphate, ester, thioester, amido, nitro, monovalent hydrocarbon, organoxy, organoamino, organosilyl, organothio, acyl and sulfone groups, and halogen atoms.

Specific examples of the monovalent hydrocarbon group include alkyl groups such as methyl, ethyl, n-propyl, i-propyl, n-butyl, i-butyl, t-butyl, n-hexyl, n-octyl, 2-ethylhexyl and decyl; cycloalkyl groups such as cyclopentyl and cyclohexyl; bicycloalkyl groups such as bicyclohexyl; alkenyl groups such as vinyl, 1-propenyl, 2-propenyl, isopropenyl, 1-methyl-2-propenyl, 1, 2 or 3-butenyl and hexenyl; aryl groups such as phenyl, xylyl, tolyl, biphenyl and naphthyl; aralkyl groups such as benzyl, phenylethyl and phenylcyclohexyl; and those formed by substituting some or all of the hydrogen atoms of these monovalent hydrocarbon groups with halogen atoms, hydroxyl groups, alkoxy groups, sulfonic acid groups and the like.

Specific examples of the organoxy group include alkoxy, alkenyloxy and aryloxy groups. The alkyl, alkenyl and aryl groups in these organoxy groups can be similar to the substituent groups exemplified above.

Specific examples of the organoamino group include alkylamino groups such as methylamino, ethylamino, propylamino, butylamino, pentylamino, hexylamino, heptylamino, octylamino, nonylamino, decylamino and laurylamino; dialkylamino groups such as dimethylamino, diethylamino, dipropylamino, dibutylamino, dipentylamino, dihexylamino, diheptylamino, dioctylamino, dinonylamino and didecylamino; dicycloalkylamino groups such as dicyclohexylamino; and morpholino group.

Specific examples of the organosilyl group include trimethylsilyl, triethylsilyl, tripropylsilyl, tributylsilyl, tripentylsilyl, trihexylsilyl, pentyldimethylsilyl, hexyldimethylsilyl, octyldimethylsilyl, and decyldimethylsilyl.

Specific examples of the organothio group include alkylthio groups such as methylthio, ethylthio, propylthio, butylthio, pentylthio, hexylthio, heptylthio, octylthio, nonylthio, decylthio and laurylthio.

Specific examples of the acyl group include formyl, acetyl, propionyl, butyryl, isobutyryl, valeryl, isovaleryl and benzoyl.

The number of carbon atoms in each of the above-described monovalent hydrocarbon, organoxy, organoamino, organosilyl, organothio, acyl and like groups may be 1 to 20 in general, with a range of from 1 to 8 being preferred, although no particular limitation is imposed thereon.

Among the above-mentioned substituents, more preferred are a fluorine atom and sulfonic acid, substituted or unsubstituted organoxy, alkyl and organosilyl groups.

It is to be noted that the term "unsubstituted" means the bonding of a hydrogen atom. It is also to be noted that in the above substituent groups, the substituent groups may be fused together to include a cyclic part.

X represents O, S or NH, with 0 being preferred.

B represents an unsubstituted or substituted hydrocarbon group, a 1,3,5-triazine group, or an unsubstituted or substituted group represented by the following formula (3) or (4):

[Chemical Formula 3]

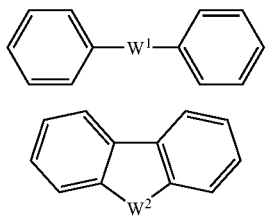

(3)

(4)

wherein $W^1$ and $W^2$ each independently represents O, S, an S(O) group, an $S(O_2)$ group, or an unsubstituted or substituted N, Si, P or P(O) group.

To achieve improvements in durability and charge transport ability, B may be preferably an unsubstituted or substituted hydrocarbon group with one or more aromatic rings contained therein, a divalent or trivalent 1,3,5-triazine group or a substituted or unsubstituted, divalent diphenylsulfone group, notably a divalent or trivalent, substituted or unsubstituted benzyl group, a divalent, substituted or unsubstituted p-xylylene group, a divalent or trivalent, substituted or unsubstituted naphthyl group, a divalent or trivalent 1,3,5-triazine group, a divalent, substituted or unsubstituted diphenylsulfone group, a di- to tetra-valent, perfluorobiphenyl group, a divalent, substituted or unsubstituted 2,2-bis((hydroxypropoxy)phenyl)propyl group, or a substituted or unsubstituted polyvinylbenzyl group.

n indicates a number of sulfonic acid group(s) bonded to A which is an aryl skeleton, and no particular limitation is imposed thereon insofar as it satisfies $1 \leq n \leq 4$. To impart high electron-accepting ability and high solubility to the compound, n may preferably be one or two.

q indicates a number of B—X bond(s), and no particular limitation is imposed thereon insofar as it stands for an integer satisfying $1 \leq q$. It is, however, preferred that q satisfies $2 \leq q$.

r indicates a number of recurring unit(s), and no particular limitation is imposed thereon insofar as it stands for an integer satisfying $1 \leq r$. It is, however, preferred that r satisfies $2 \leq r$.

As a method for the production of the arylsulfonic acid compound represented by the formula (1) or (2), the following methods can be mentioned as an example.

Described specifically, it can be obtained by causing a (crosslinking) reagent, which can introduce the above-mentioned B, to act on the group XH in the below-described arylsulfonic acid compound (5) or (6). No particular limitation is imposed on the manner of the reaction. For example, a general nucleophilic substitution reaction may be employed.

[Chemical Formula 4]

(5)

(6)

Such a reagent can be a hydrocarbon compound or the like, which is substituted by a halogen atom or a hydroxyl, amino, aldehyde, carboxyl, ester or alkoxy group. As mentioned above in the description of B, such a compound may preferably contain one or more aromatic rings from the standpoint of making improvement(s) in heat resistance, charge transport ability and/or the solubility in an organic solvent.

Further, use of a hydrocarbon compound containing two or more substituents such as halogen atoms and/or hydroxyl, amino, aldehyde, carboxyl, ester and/or alkoxy groups can form a compound having a crosslinked structure because the hydrocarbon compound acts as a crosslinking reagent. Upon q-merizing the compound of the formula (5) with a reagent having q or more reactive substituent groups (crosslinking sites), the reagent may be used preferably in a molar amount as little as 1/q times the compound of the formula (5).

Examples of the reagent to be reacted with the group XH in the arylsulfonic acid compound (5) or (6) include benzaldehyde, benzoic acid, benzoate esters, 1-naphthaldehyde, 2-naphthaldehyde, 2,4,6-trimethoxy-1,3,5-triazine, bis(4-fluorophenyl)sulfone, bis(4-fluoro-3-nitrophenyl)sulfone, perfluorobiphenyl, 2,2-bis(4-glycidyloxyphenyl)propane, and polyvinylbenzyl chloride.

When reacting the arylsulfonic acid compound (5) or (6) with the above-described reagent, a catalyst may be used.

Usable examples of the catalyst include bases such as lithium, potassium, lithium hydride, sodium hydride, t-butoxylithium, t-butoxysodium, t-butoxypotassium, lithium diisopropylamide, n-butyllithium, s-butyllithium, t-butyllithium, lithium hexamethyldisilazide, sodium hexamethyldisilazide, potassium hexamethyldisilazide, lithium hydroxide, sodium hydroxide, potassium hydroxide, barium hydroxide, barium oxide, lithium carbonate, sodium carbonate, potassium carbonate, cesium carbonate, calcium carbonate, sodium hydrogencarbonate, triethylamine, diisopropylethylamine, tetramethylethylenediamine, triethylenediamine, pyridine, dimethylaminopyridine and imidazole; and dehydration condensing agents such as hydrochloric acid, sulfuric acid, diphosphorus pentoxide, aluminum (III) chloride, boron trifluoride-diethyl ether complex, ethylaluminum dichloride and diethylaluminum chloride. Of these, sodium hydride, sodium carbonate and potassium carbonate are preferred. Although no particular limitation is imposed on the amount of such a catalyst to be used, it is preferred to use the catalyst as much as 1.0 to 1.5 molar times the compound of the formula (5) or (6).

The reaction solvent may preferably be an aprotonic polar organic solvent. Preferred examples include DMF, DMAc, NMP, DMI, DMSO, THF, and dioxane. Among these solvents, DMI and NMP are suited, because the arylsulfonic acid compound has low solubility in organic solvents so that solvents having high dissolving power for the compound and low decomposition property are preferred.

The reaction temperature may range generally from $-50°$ C. to the boiling point of the solvent, but a range of from 0 to 140° C. is preferred. The reaction time may range from 0.1 to 100 hours in general.

After the completion of the reaction, the reaction product can be purified by distilling off the reaction solvent, protonizing the sulfonate salt with a cation exchange resin, conducting extraction with a solvent such as methanol, and effecting reprecipitation or the like.

As another synthesis method for the arylsulfonic acid compound of the present invention represented by the formula (1) or (2), the arylsulfonic acid compound can be obtained by a general sulfonation reaction that uses concentrated sulfuric acid, fuming sulfuric acid or a halosulfuric acid for the aryl compound.

The arylsulfonic acid compound of the invention represented by the formula (1) may also be crosslinked with a compound, which contains a crosslinking group, into an arylsulfonic acid compound represented by the following formula (7):

[Chemical Formula 5]

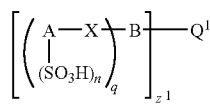
(7)

wherein A, B, X, n and q have the same meanings as described above, $Q^1$ represents a hydrogen atom, a halogen atom, S, an S(O) group, an S(O$_2$) group, an unsubstituted or substituted N, Si, P, P(O) group, an unsubstituted or substituted hydrocarbon group, a 1,3,5-triazine group, or a substituted or unsubstituted group represented by the above-described formula (3) or (4), $z^1$ stands for an integer which is equal to the valence number of $Q^1$ and satisfies $1 \leq z^1$.

Specifically, it is preferred to effect the crosslinking with resorcinol, fluoroglucinol, 2,2-bis(4-hydroxyphenyl)hexafluoropropane, octafluoro-4,4-biphenol, (1,1'-biphenyl)-4,4'-diol, 4,4'-ethylidenebisphenol, 4,4'-cyclohexylidenebisphenol, 4,4'-cyclopentylidenebisphenol, 4,4'-(phenylmethylene)bisphenol, 4,4'-(1-phenylethylidene)bisphenol, 4,4'-methylenebisphenol, 4,4'-(2-methylpropylidene)bisphenol, 4,4'-methylenebis(2-fluorophenol), 4,4'-isopropylidenebis(2-fluorophenol), 4,4'-[(4-fluorophenyl)methylene]bis(2-fluorophenol), 4,4'-[2,2,2-trifluoro-1-(trifluoromethyl)ethylidene]bisphenol, 4,4'-(diphenylmethylene)bisphenol, 4,4'-dihydroxy-p-terphenyl, 4,4'-oxybisphenol, 4,4'-(diphenylsilylene)bisphenol, or the like.

The arylsulfonic acid compound of the invention represented by the formula (1) can also be crosslinked with a high-molecular compound, which has crosslinking groups, into an arylsulfonic acid compound represented by the below-described formula (8) or (9). In this case, poly(4-hydroxystyrene), novolak resins and the like can be mentioned as suitable high-molecular crosslinking agents.

[Chemical Formula 6]

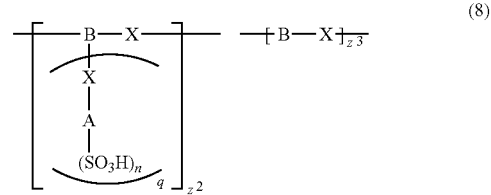
(8)

wherein A, B, X, n and q have the same meanings as described above, $z^2$ stands for an integer satisfying $1 \leq z^2$, $z^3$ stands for an integer satisfying $0 \leq z^3$, and $z^2$ and $z^3$ satisfy $1 \leq z^2 + z^3 \leq 10,000$.

[Chemical Formula 7]

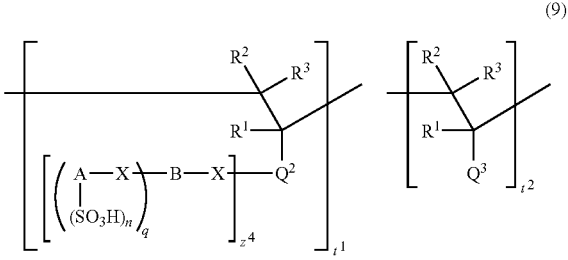
(9)

wherein A, B, X, n and q have the same meanings as described above, $R^1$ to $R^3$ each independently represents a hydrogen atom, an unsubstituted or substituted, monovalent hydrocarbon group or a halogen atom, $Q^2$ represents an unsubstituted or substituted, divalent or higher hydrocarbon group, a divalent or trivalent 1,3,5-triazine group or a substituted or unsubstituted group represented by the above-described formula (3) or (4), $Q^3$ represents an unsubstituted or substituted, monovalent hydrocarbon group, a 1,3,5-triazine group or a substituted or unsubstituted group represented by the above-described formula (3) or (4), $z^4$ stands for an integer which is equal to (the valence of $Q^2-1$) and satisfies $1 \leq z^4$, $t^1$ stands for an integer satisfying $1 \leq t^1$, $t^2$ stands for an integer satisfying $0 \leq t^2$, and $t^1$ and $t^2$ satisfy $1 \leq t^1 + t^2 \leq 10,000$.

The arylsulfonic acid compounds represented by the formula (1), (2) and (6) to (9), respectively, have electron-accepting ability, and can be suitably used as electron acceptor materials.

In the present invention, the charge-transporting varnish contains in a solvent at least two materials, one being a charge-transporting material as a main component in a charge transport system, and the other an electron acceptor material represented by any one of the formulas (1), (2) and (6) to (9). The electron acceptor substance is used to make improvements in charge transport ability and uniform film-forming ability, and is synonymous with a charge-accepting dopant material.

In the charge-transporting varnish of the invention, these materials may be fully dissolved or evenly dispersed in the solvent.

The term "charge transport ability" is synonymous with electrical conductivity, and in the present invention, is synonymous with hole transport ability. The charge-transporting varnish may have the charge transport ability or a solid film obtained from the varnish may have the charge transport ability.

No particular limitation is imposed on the charge-transporting material useful in the invention insofar as it is a charge-transporting oligomer or polymer soluble or evenly dispersible in a solvent. Nonetheless, an oligomer having successive conjugate units of the same kind or an oligomer having a combination of successive conjugate units of different kinds is desired.

No particular limitation is imposed on the conjugate units insofar as they are atoms, aromatic rings or conjugate groups capable of transporting a charge. Preferred examples include substituted or unsubstituted, di- to tetra-valent, aniline groups, thiophene groups, furan groups, pyrrole groups, ethynylene groups, vinylene groups, phenylene groups, naphthalene groups, oxadiazole groups, quinoline groups, silole groups, silicon atoms, pyridine groups, phenylvinylene groups, fluorene groups, carbazole groups, triarylamine groups, metal- or nonmetal-phthalocyanine groups, and metal- or nonmetal-porphyrin groups.

Specific examples of the substituents are each independently a hydrogen atom, hydroxyl group, halogen atom, amino group, silanol group, thiol group, carboxyl group, sulfonic acid group, phosphoric acid group, phosphate ester group, ester group, thioester group, amido group, nitro group, monovalent hydrocarbon group, organoxy group, organoamino group, organosilyl group, organothio group, acyl group, or sulfone group. These functional groups may each be substituted further with any of these functional groups.

Specific examples of the monovalent hydrocarbon group include alkyl groups such as methyl, ethyl, n-propyl, i-propyl, n-butyl, i-butyl, t-butyl, n-hexyl, n-octyl, 2-ethylhexyl and decyl; cycloalkyl groups such as cyclopentyl and cyclohexyl; bicycloalkyl groups such as bicyclohexyl; alkenyl groups such as vinyl, 1-propenyl, 2-propenyl, isopropenyl, 1-methyl-2-propenyl, 1-, 2- or 3-butenyl and hexenyl; aryl groups such as phenyl, xylyl, tolyl, biphenyl and naphthyl; aralkyl groups such as benzyl, phenylethyl and phenylcyclohexyl; and those formed by substituting some or all of the hydrogen atoms of these monovalent hydrocarbon groups with halogen atoms, hydroxyl groups, alkoxy groups, and/or the like.

Specific examples of the organoxy group include alkoxy, alkenyloxy and aryloxy groups. The alkyl, alkenyl and aryl groups in these organoxy groups can be similar to the groups exemplified above.

Specific examples of the organoamino group include alkylamino groups such as methylamino, ethylamino, propylamino, butylamino, pentylamino, hexylamino, heptylamino, octylamino, nonylamino, decylamino and laurylamino; dialkylamino groups such as dimethylamino, diethylamino, dipropylamino, dibutylamino, dipentylamino, dihexylamino, diheptylamino, dioctylamino, dinonylamino and didecylamino; cycloalkylamino groups such as cyclohexylamino; and morpholino group.

Specific examples of the organosilyl group include trimethylsilyl, triethylsilyl, tripropylsilyl, tributylsilyl, tripentylsilyl, trihexylsilyl, pentyldimethylsilyl, hexyldimethylsilyl, octyldimethylsilyl, and decyldimethylsilyl.

Specific examples of the organothio group include alkylthio groups such as methylthio, ethylthio, propylthio, butylthio, pentylthio, hexylthio, heptylthio, octylthio, nonylthio, decylthio and laurylthio.

Specific examples of the acyl group include formyl, acetyl, propionyl, butyryl, isobutyryl, valeryl, isovaleryl and benzoyl.

The number of carbon atoms in each of the above-described monovalent hydrocarbon, organoxy, organoamino, organosilyl, organothio, acyl and like groups may be 1 to 20 in general, with a range of from 1 to 8 being preferred, although no particular limitation is imposed thereon.

Preferred substituents are a fluorine atom and sulfonic acid, substituted or unsubstituted organoxy, alkyl and organosilyl groups. It is to be noted that a conjugate chain formed of conjugate units bonded together may contain a cyclic part.

The number average molecular weight of the charge-transporting material may desirably be 5,000 or lower from the standpoint of providing higher solubility, but to show low volatility and charge transport ability, it may desirably be 200 or higher. A charge-transporting material showing high solubility in at least one solvent is preferred. A charge-transporting material may have a number average molecular of from 5,000 to 500,000 provided that it shows high solubility in at least one solvent.

As a charge-transporting material, the use of an oligoaniline derivative disclosed in JP-A 2002-151272 is particularly suited. Described specifically, an oligoaniline derivative represented by the following formula (10) is suited. It is to be noted that the following monovalent hydrocarbon group, organoxy group and acyl groups represented by $R^7$ to $R^{14}$ can be similar to the substituent groups exemplified above.

[Chemical Formula 8]

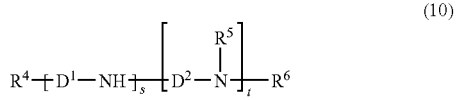

(10)

wherein $R^4$ represents a hydrogen atom, a monovalent hydrocarbon group or an organoxy group, $R^5$ and $R^6$ each independently represents a hydrogen atom or a monovalent hydrocarbon group, $D^1$ and $D^2$ each independently represents a divalent group represented by the following formula (11) or (12):

[Chemical Formula 9]

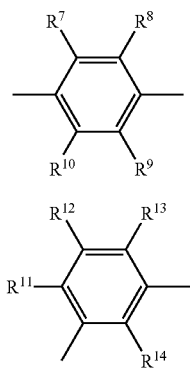

wherein $R^7$ to $R^{14}$ each independently represents a hydrogen atom, a hydroxyl group, a monovalent hydrocarbon group, an organoxy group, an acyl group or a sulfonic acid group, and s and t each independently stands for an integer of one or greater and satisfy s+t≦20.

It is desired to expand the π conjugated system as much as possible in the molecule because the resulting charge-transporting thin film is provided with improved charge transport ability. It is particularly preferred to use an oligoaniline derivative represented by the below-described formula (13) or its oxidation product, i.e., a quinonediimine derivative. It is to be noted that in the two benzene rings in the formula (13), the substituents represented by the same sign may be identical at the same time or may be different.

[Chemical Formula 10]

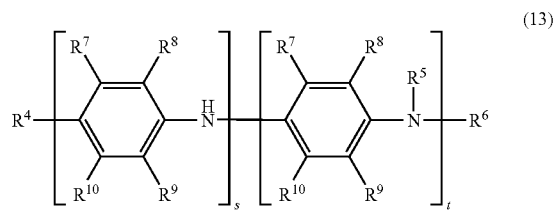

wherein $R^4$ to $R^{10}$, s and t have the same meanings as described above.

In the formulas (10) and (13), s+t may preferably be four or greater from the standpoint of exhibiting good charge transport ability, but may preferably be 16 or smaller from the standpoint of assuring solubility in a solvent.

It is preferred that $R^4$ is a hydrogen atom and $R^6$ is a phenyl group, in other words, the oligoaniline derivative of the formula (13) are capped at both ends thereof with phenyl groups.

These charge-transporting materials can be used either singly or in any combination.

Specific examples of the compound represented by the formula (13) include oligoaniline derivatives soluble in organic solvents such as phenyltetraaniline, phenylpentaaniline, tetraaniline (aniline tetramer) and octaaniline (aniline octamer).

Examples of other synthesis methods for the charge-transporting material include, but are not limited to, the oligoaniline synthesis method described in the publications, Bulletin of Chemical Society of Japan, Vol. 67, pp. 1749-1752 (1994) and Synthetic Metals, Vol. 84, pp. 119-120, U.S.A. (1997) and the oligothiophene synthesis method described in the publications, Heterocycles, Vol. 26, pp. 939-942 (1987) and Hetrocycles, Vol. 26, pp. 1793-1796 (1987).

In the charge-transporting varnish of the invention, a high-solubility solvent which can dissolve the charge-transporting material and the charge acceptor material well may be used in a proportion of from 5 to 100 wt % based on the whole solvent employed in the varnish. In this case, the varnish is preferably in a state completely dissolved or evenly dispersed with the high-solubility solvent.

Examples of the high-solubility solvent include, but are not specifically limited to, water, methanol, N,N-dimethylformamide, N,N-dimethylacetamide, N-methylpyrrolidone, N,N'-dimethylimidazoline, dimethyl sulfoxide, chloroform, toluene, and methanol.

Further, the charge-transporting varnish of the invention may desirably contain at least one high-viscosity organic solvent having a viscosity of from 10 to 200 mPa·s at 20° C. and a boiling point of from 50 to 300° C. under normal pressure. It is also preferred to the charge-transporting varnish to contain an organic solvent having a viscosity of from 50 to 150 mPa·s at 20° C. and a boiling point of from 150 to 250° C. under normal pressure.

Examples of the high-viscosity organic solvent include, but are not specifically limited to, cyclohexanol, ethylene glycol, ethylene glycol diglycidyl ether, 1,3-octylene glycol, diethylene glycol, dipropylene glycol, triethylene glycol, tripropylene glycol, 1,3-butanediol, 1,4-butanediol, propylene glycol, and hexylene glycol.

The proportion of the added high-viscosity organic solvent based on the whole solvent employed in the varnish of the invention may preferably be within such a range as causing no precipitation of solid, and its proportion may range from 5 to 80 wt % insofar as no solid precipitate.

For the purpose of improving the wettability to substrates or adjusting the surface tension, polarity and/or boiling point of the solvent, a further solvent capable of imparting levelness to a resulting film upon firing can be mixed in a proportion of from 1 to 90 wt %, preferably from 1 to 50 wt % based on the whole solvent to be employed in the varnish.

Examples of such a solvent include, but are not specifically limited to, butyl cellosolve, diethylene glycol diethyl ether, dipropylene glycol monomethyl ether, ethyl carbitol, diacetone alcohol, γ-butyrolactone, and ethyl lactate.

A charge-transporting thin film can be formed on a substrate by coating the above-described charge-transporting varnish on the substrate and evaporating the solvent.

The coating process of the varnish can be, but is not specifically limited to, dip coating, spin coating, spray coating, inkjet coating, transfer printing, roll coating, brush coating or the like. Formation of a uniform film is feasible by any one of these coating processes.

Although no particular limitation is imposed on the evaporation method of the solvent, a film having a uniform film surface can be obtained by conducting the evaporation in a suitable atmosphere, namely, in air, an inert gas such as nitrogen or in a vacuum with a hot plate or in an oven.

No particular limitation is imposed on the baking temperature insofar as the solvent can be evaporated. Preferably, however, the baking can be conducted at 40 to 250° C. To exhibit still higher uniform film-forming property or to allow a reaction to proceed on the substrate, the baking may be conducted by changing the temperature at two or more stages.

No particular limitation is imposed on the thickness of the charge-transporting film obtained by the coating and evaporation operations. When it is used as a charge injection layer in an organic EL device, however, the film thickness may desirably be 5 to 200 nm. As a method for changing the film thickness, the solid concentration of the varnish can be changed, or upon coating, the amount of the varnish to be applied onto the substrate can be changed.

As a method for fabricating OLED devices by using the charge-transporting varnish of the invention and materials to be used in the method, the following method and materials can be mentioned although the invention is not limited to them.

An electrode substrate to be used is cleaned beforehand by washing it with a liquid such as a detergent, an alcohol or purified water. In the case of an anode substrate, it is preferred to conduct surface treatment such as ozone treatment or oxygen-plasma treatment shortly before use. Such surface treatment may, however, be omitted when the anode material is primarily composed of an organic material.

When a hole-transporting varnish is used for OLED devices, the following method may be adopted as an example.

Using the hole-transporting varnish for an anode substrate, a hole-transporting thin film is formed on electrodes by the above-described film-forming method. The anode substrate with the hole-transporting thin film formed thereon is introduced into a vacuum evaporation system, and a hole transport layer, a light-emitting layer, an electron transport layer, an electron injection layer and a cathode metal are successively evaporated to fabricate the OLED devices. In the course of the fabrication, a carrier block layer may be arranged between desired layers to control light-emitting regions.

As the anode material, a transparent electrode material led by indium-tin oxide (ITO) or indium-zinc oxide (IZO) can be mentioned, with one subjected to leveling treatment being preferred. It is also possible to use a polythiophene derivative or polyaniline having high charge transport ability.

Illustrative of a material for forming the hole transport layer are triarylamines such as (triphenylamine) dimer derivatives (TPDs), (α-naphthyldiphenylamine)dimer (α-NPD) and [(triphenylamine)dimer]spirodimer (Spiro-TAD); starburst amines such as 4,4',4''-tris[3-methylphenyl (phenyl)amino]triphenylamine (m-MTDATA) and 4,4',4''-tris[1-naphthyl(phenyl)amino]triphenylamine (1-TNATA); and oligothiophenes such as 5,5''-bis-{4-[bis(4-methylphenyl)amino]phenyl}-2,2':5',2''-terthiophene (BMA-3T).

Illustrative of a material for forming the light-emitting layer are tris(8-quinolinolato)aluminum(III) ($Alq_3$), bis(8-quinolinolato)zinc(II) ($Znq_2$), bis(2-methyl-8-quinolinolato) (p-phenylphenolato) aluminum(III) (BAlq), and 4,4'-bis(2,2-diphenylvinyl)biphenyl (DPVBi).

The light-emitting layer may be formed by coevaporating an electron-transporting material or hole-transforming material and a light-emitting dopant.

Illustrative of the electron-transporting material are $Alq_3$, BAlq, DPVBi, (2-(4-biphenyl)-5-(4-t-butylphenyl)-1,3,4-oxadiazole) (PBD), triazole derivatives (TAZs), bathocuproin (BCP), and silole derivatives.

Illustrative of the light-emitting dopant are quinacridone, rubrene, coumarin 540, 4-(dicyanomethylene)-2-methyl-6-(p-dimethylaminostyryl)-4H-pyran (DCM), tris(2-phenylpyridine)iridium(III) ($Ir(ppy)_3$), and (1,10-phenanthroline)-tris (4,4,4-trifluoro-1-(2-thenyl)butane-1,3-dionate)europium (III) ($Eu(TTA)_3$-phen).

Illustrative of a material for forming the carrier block layer are PBD, TAZ, and BCP.

Illustrative of a material for forming the electron injection layer are lithium oxide ($Li_2O$), magnesium oxide (MgO), alumina ($Al_2O_3$), lithium fluoride (LiF), magnesium fluoride ($MgF_2$), strontium fluoride ($SrF_2$), lithium quinolide (Liq), lithium-acetyl acetonate complex (Li(acac)), lithium acetate, and lithium benzoate.

Illustrative of the cathode metal are aluminum, magnesium-silver alloy, aluminum-lithium alloy, lithium, sodium, potassium, and cesium.

When the charge-transporting varnish of the invention is used for OLED devices, the following method may be adopted as an example.

Using the electron-transporting varnish, an electron-transporting thin film is formed on a cathode substrate. The cathode substrate with the electron-transporting thin film formed thereon is introduced into a vacuum evaporation system. After forming an electron transport layer, a light-emitting layer, a hole transport layer and a hole injection layer with similar materials as described above, an anode material is formed into a film by sputtering or a like method to fabricate OLED devices.

As a process for fabricating PLED devices by using the charge-transporting varnish of the invention, the following method can be mentioned although the present invention is not limited to it.

By forming a light-emitting, charge-transporting high-molecular layer instead of conducting the vacuum evaporation of the hole transport layer, light-emitting layer, electron transport layer and electron injection layer in the above-described fabrication of the OLED devices, the PLED devices can be fabricated each including a charge-transporting thin film formed with the charge-transporting varnish of the invention.

Specifically, the hole-transporting varnish is coated on an anode substrate by the above-described method to form a hole-transporting thin film on electrodes. Over the hole-transporting thin film, a light-emitting, charge-transporting high-molecular layer is formed, and cathode electrodes are then evaporation-deposited to fabricate the PLED devices.

As an alternative, using the electron-transporting varnish for a cathode substrate, an electron-transporting thin film is formed on electrodes by the above-described method. Over the electron-transporting thin film, a light-emitting, charge-transporting high-molecular layer is formed, and anode electrodes are then formed by sputtering, evaporation, spin coating or the like to fabricate the PLED devices.

As cathode and anode materials, materials similar to those exemplified above with respect to the OLED devices can be used, and washing treatment and surface treatment can be conducted likewise.

As a method for forming the light-emitting, charge-transporting high-molecular layer, there San be mentioned a method which comprises adding a solvent to a light-transmitting, charge-transporting high-molecular material or a material obtained by adding a light-emitting dopant to the light-transmitting, charge-transporting high-molecular material, dissolving or evenly dispersing the material, coating the dispersion onto an electrode substrate having a hole-transporting thin film formed thereon, and then evaporating the solvent to form a film.

Illustrative of the light-emitting, charge-transporting high-molecular material are polyfluorene derivatives such as poly (9,9-dialkylfluorene) (PDAF), polyphenylenevinylene derivatives such as poly(2-methoxy-5-(2'-ethylhexoxy)-1,4-phenylenevinylene) (MEH-PPV), polythiophene derivatives such as poly(3-alkylthiophene) (PAT), and polyvinylcarbazole (PVCz).

Illustrative of the solvent are toluene, xylene, and chloroform. As a dissolution or even dispersion method, there can be mentioned a method for effecting dissolution or even dispersion by a method such as stirring, stirring under heat, or ultrasonic dispersion.

As a coating process, dip coating, spin coating, transfer printing, roll coating, brush coating or a like coating process can be mentioned, although no particular limitation is imposed on it. It is desired to conduct the coating under an inert gas such as nitrogen or argon.

As a method for evaporating the solvent, there can be mentioned a method which comprises heating with an oven or hot plate under an inert gas or in a vacuum.

EXAMPLES

The present invention will hereinafter be described more specifically based on Synthesis Examples, Examples and Comparative Examples. It should, however, be borne in mind that the present invention is not limited to the following Examples.

Example 1

According to the reaction scheme (14) below, a naphthalenedisulfonic acid compound oligomer 1 (hereinafter abbreviated as "NSO-1") was synthesized.

[Chemical Formula 11]

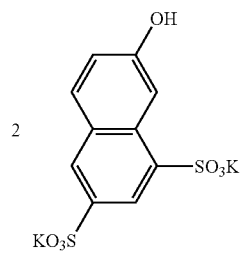

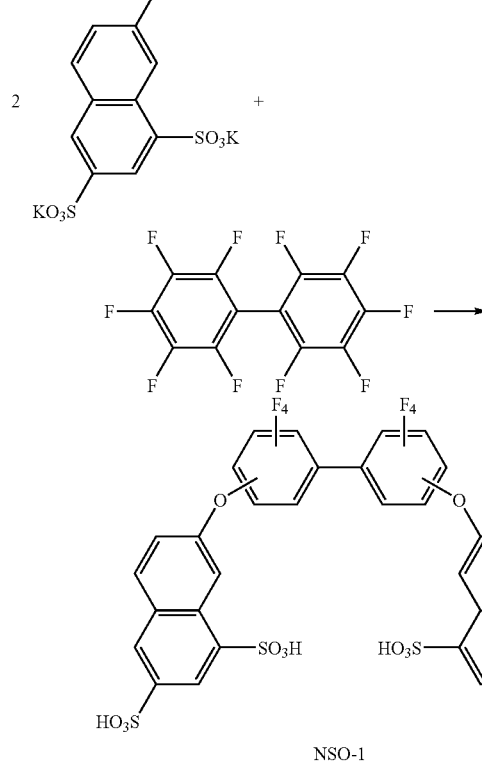

Described specifically, perfluorobiphenyl (449 mg), 60% sodium hydride (161 mg) and anhydrous N,N-dimethylimidazolidinone (50 mL) were successively added under a nitrogen atmosphere to dipotassium 2-naphthol-6,8-disulfonate (product of Tokyo Chemical Industry Co., Ltd., 1.020 g) which had been dried thoroughly. After the reaction system was purged with nitrogen, the resulting mixture was stirred at 80° C. for 43 hours.

The reaction mixture was allowed to cool down to room temperature, followed by the addition of water to terminate the reaction. The reaction mixture was then concentrated to dryness under reduced pressure. Methanol (5 mL) was added to the residue, and the thus-obtained suspension was added to diethyl ether (100 mL) under stirring. Subsequent to stirring at room temperature for one hour, the precipitated solid was collected by filtration. Methanol (50 mL) was added to the filter cake, followed by ultrasonication into a suspension. Insoluble solid was filtered off, and the filtrate was concentrated to dryness under reduced pressure. Purified water (3 mL) was added to the residue to dissolve the same. A cation exchange resin "DOWEX 650C" (hydrogen form, about 2 mL) was added to the resultant solution. The resultant mixture was stirred for 10 minutes, and was then filtered. By column chromatography making use of the cation exchange resin "DOWEX 650C" (hydrogen form, about 40 mL, eluent: acetonitrile-water (1:10)), the filtrate was purified.

Fractions lower than pH 1 were concentrated to dryness under reduced pressure. After azeotropically boiled once in isopropanol, isopropanol (2 mL) was added to the residue, and the thus-obtained solution was added into diethyl ether (50 mL) under stirring. After the resultant mixture was stirred at room temperature for 1 hour, the supernatant was decanted, and the residue was dried under reduced pressure to afford a yellow powder (1.043 g, yield: 86%).

The yellow powder was analyzed by MALDI-TOF-MS. As a result, a main peak considered to be derived from NSO-1 was detected.

MS (MALDI-TOF-MS-): m/z 901 (M-H)⁻

Example 2

According to the reaction scheme (15) below, a naphthalenedisulfonic acid compound oligomer 2 (hereinafter abbreviated as "NSO-2") was synthesized.

[Chemical Formula 12]

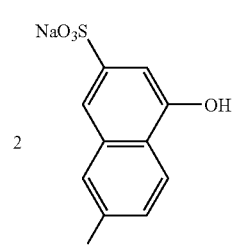

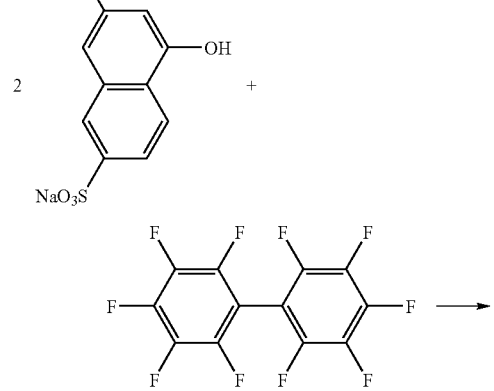

-continued

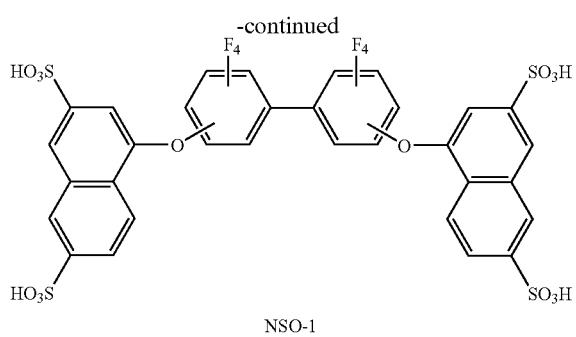

NSO-1

Described specifically, perfluorobiphenyl (450 mg), 60% sodium hydride (166 mg) and anhydrous N,N-dimethylimidazolidinone (50 mL) were successively added under a nitrogen atmosphere to sodium 1-naphthol-3,6-disulfonate (product of Tokyo Chemical Industry Co., Ltd., 934 mg) which had been dried thoroughly. After the reaction system was purged with nitrogen, the resulting mixture was stirred at 80° C. for 43 hours.

The reaction mixture was allowed to cool down to room temperature, followed by the addition of water to terminate the reaction. The reaction mixture was then concentrated to dryness under reduced pressure. Methanol (5 mL) was added to the residue, and the thus-obtained suspension was added to diethyl ether (100 mL) under stirring. Subsequent to stirring at room temperature for 1 hour, the precipitated solid was collected by filtration. Methanol (25 mL) was added to the filter cake, followed by ultrasonication into a suspension. Insoluble solid was filtered off, and the filtrate was concentrated to dryness under reduced pressure. Methanol-water (1:2, 12 mL) was added to the residue to dissolve the same. The cation exchange resin "DOWEX 650C" (hydrogen form, about 2 mL) was added to the resultant solution. The resultant mixture was stirred for 10 minutes, and was then filtered. By column chromatography making use of the cation exchange resin "DOWEX 650C" (hydrogen form, about 40 mL, eluent: methanol-water (1:2)), the filtrate was purified.

Fractions lower than pH 1 were concentrated to dryness under reduced pressure. After azeotropically boiled once in isopropanol, isopropanol (2 mL) was added to the residue, and the thus-obtained solution was added into diethyl ether (50 mL) under stirring. After the resultant mixture was stirred at room temperature for 1 hour, the supernatant was decanted, and the residue was dried under reduced pressure to afford a yellow powder (984 mg, yield: 81%).

The yellow powder was analyzed by MALDI-TOF-MS. As a result, a main peak considered to be derived from NSO-2 was detected.

MS (MALDI-TOF-MS-): m/z 90.1 (M-H)⁻

Synthesis Example 1

Synthesis of Phenyltetraaniline

[Chemical Formula 13]

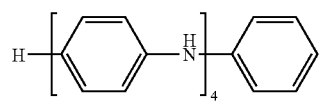

(16)

Based on the process described in Bulletin of Chemical Society of Japan, 67, pp. 1749-1752 (1994), phenyltetraaniline (PTA) was obtained as will be described hereinafter.

Described specifically, p-phenylenediamine (12.977 g) was dissolved in toluene (2 L). To the resulting solution, tetra-n-butoxytitanium (245.05 g) was added as a dehydration condensing agent, followed by dissolution at 70° C. for 30 minutes. p-Hydroxydiphenylamine (53.346 g) was then added, and under a nitrogen atmosphere, was reacted at a reaction temperature of 100° C. for 24 hours. After completion of the reaction, the reaction mixture was filtered. The filter cake was washed successively with toluene and ether, and was then dried to obtain crystals of a silver color. To the thus-obtained crystals, dioxane (25 parts by weight) and hydrazine monohydrate (0.2 equivalent) were added. After the reaction system was purged with nitrogen, the mixture was refluxed under heat to dissolve the crystals. To the resulting solution, toluene (25 parts by weigh based on the crystals) was added to convert the solution into a suspension. Subsequent to refluxing under heat, dioxane (10 parts by weight) was added further. The resulting mixture was refluxed under heat, and the thus-obtained solution was subjected to hot filtration.

The solid precipitated from the filtrate was recrystallized, was washed successively with toluene-dioxane (1:1) and ether, and was then collected by filtration. The thus-obtained crystals were dried at 60° C. for 10 hours under reduced pressure. A similar recrystallization operation was repeated once again to afford white crystals (39.60 g, yield: 75%).

Using as electron-acceptor materials the arylsulfonic acid compounds obtained in Examples 1 and 2, charge-transporting varnishes were prepared with the phenyltetraaniline (hereinafter abbreviated as "PTA") of the formula (16) contained as a charge-transporting material. The preparation procedures of those varnishes will be described in Examples 3 and 4.

Example 3

To a mixture of NSO-1 (102 mg) obtained in Example 1 and PTA (50 mg) obtained in Synthesis Example 1, N,N-dimethylformamide (hereinafter abbreviated as "DMF") was added under a nitrogen atmosphere to dissolve the mixture. Under a nitrogen atmosphere, ethylene glycol (0.49 mL) and cyclohexanol (2.77 mL) were successively added, and the resulting mixture was stirred at room temperature to obtain a clear varnish of a green color.

Example 4

To a mixture of NSO-2 (102 mg) obtained in Example 2 and PTA (50 mg) obtained in Synthesis Example 1, N,N-dimethylformamide (hereinafter abbreviated as "DMF") (1.70 mL) was added under a nitrogen atmosphere to dissolve the mixture. Under a nitrogen atmosphere, ethylene glycol (0.49 mL) and cyclohexanol (2.77 mL) were successively added, and the resulting mixture was stirred at room temperature to obtain a clear varnish of a green color.

Examples 5 & 6

After the varnishes obtained by the procedures described in Examples 3 and 4 were separately spin-coated on ITO substrates, the varnishes were baked on a hot plate to form hole-transporting thin films. The ITO substrates with the hole-transporting thin films formed thereon were each introduced into a vacuum evaporation system, and α-NPD, Alq₃, LiF and Al were successively evaporated. Their film thicknesses were controlled at 35 nm, 50 nm, 0.5 nm and 100 nm, respectively. Each evaporation operation was conducted after the pressure was reduced to $8\times10^{-4}$ Pa or lower. The evaporation rate was set at 0.35 to 0.40 nm/s for α-NPD and $Alq_3$, at 0.015 to 0.025 nm/s for LiF, and at 0.2 to 0.4 nm/s for Al. Transfer operations between the respective evaporation operations were conducted in a vacuum.

Comparative Example 1

After an ITO glass substrate was washed with ozone for 40 minutes, the ITO glass substrate was introduced into a vacuum evaporation system. Under similar conditions as in the procedure described in Example 5, α-NPD, $Alq_3$, LiF and Al were successively evaporation-deposited.

Comparative Example 2

To a mixture of (+)-10-camphorsulfonic acid (206 mg) and PTA (100 mg) obtained in Synthesis Example 1, DMAc (1.87 mL) was added under a nitrogen atmosphere to dissolve the mixture. Cyclohexanol (5.53 mL) was then added, and the resulting mixture was stirred at room temperature to obtain a clear varnish of a green color.

Using the thus-obtained varnish, a charge-transporting thin film was obtained by the procedure described in Example 5. The resultant charge-transporting film was an amorphous solid. An OLED device was then fabricated by the procedure described in Example 5.

Comparative Example 3

To PTA (1.000 g, 2.260 mmol), 5-sulfosalicylic acid dehydrate (hereinafter abbreviated as "5-SSA", 2.298 g (9.039 mmol)) and N,N-dimethylacetamide (DMAC, 17.50 g) were added under a nitrogen atmosphere, followed by dissolution. To the resulting solution, cyclohexanol (c-HexOH, viscosity: 68 mPa·s (20° C.), 52.50 g) was added, and the resulting mixture was stirred to prepare a varnish (solid concentration: 4.2 wt %).

Onto an ITO glass substrate which had been washed with ozone for 40 minutes, the thus-obtained varnish was coated by spin coating. The varnish was then baked at 180° C. for two hours in air to obtain a uniform thin film.

The ITO glass substrate with the thin film formed thereon was introduced into a vacuum evaporation system, and α-NPD, $Alq_3$, LiF and Al were successively evaporated. Their film thicknesses were controlled at 40 nm, 60 nm, 0.5 nm and 100 nm, respectively. Each evaporation operation was conducted after the pressure was reduced to $8\times10^{-4}$ Pa or lower. Except for LiF, the evaporation rate was set at 0.3 to 0.4 nm/s. For LiF, the evaporation rate was set at 0.02 to 0.04 nm/s. Transfer operations between the respective evaporation operations were conducted in a vacuum. Characteristics of the thus-obtained OLED device are shown in Table 2.

The viscosities, baking conditions, film thicknesses and $I_p$ values of the varnishes used in Examples 5 and 6 and Comparative Example 2 are shown in Table 1, while characteristics of the OLED devices fabricated in Examples 5 and 6 and Comparative Examples 1 to 3 are shown in Table 2.

Each film thickness, $I_p$ value, electrical conductivity, EL characteristic and viscosity were measured by the following instruments:

[1] Film Thickness:
Measured with a surface profiler ("DEKTAK3ST", manufactured by Japan Vacuum Technology Co., Ltd.).

[2] $I_p$ Value:
Measured with a photoelectron spectrometer ("AC-2", manufactured by Riken Keiki Co., Ltd.).

[3] EL Measurement System:
Luminescence efficiency measurement system ("EL1003", Precise Gauges Co., Ltd.).

[4] Voltmeter (Voltage Generation Source):
Programmable d.c. voltage/current source ("R6145", manufactured by Advantest Corporation).

[5] Ammeter:
Digital multimeter ("R6581D", manufactured by Advantest Corporation).

[6] Brightness Meter:
"LS-110" (manufactured by Konica Minolta Holdings. Inc.).

[7] Viscometer:
Cone-plate type, rotational viscometer ("ELD-50", manufactured by Tokyo Keiki Co., Ltd.), measurement temperature: 20° C.

TABLE 1

|  | Varnish | Solid content [wt %] | Viscosity [mPa·s] | Baking conditions | Film thickness [nm] | $I_p$ |
| --- | --- | --- | --- | --- | --- | --- |
| Example 5 | Example 3 | 2.1 | 9.0 | 220° C., 15 min | 18 | 5.46 |
|  | Example 3 | 2.1 | 9.0 | 220° C., 15 min | 24 | 5.46 |
| Example 6 | Example 4 | 2.1 | 9.0 | 220° C., 15 min | 18 | 5.55 |
|  | Example 4 | 2.1 | 9.0 | 220° C., 15 min | 26 | 5.56 |
| Comparative Example 2 |  | 4.2 | 11.5 | 180° C., 2 hr | 12 | 5.49 |
|  |  | 4.2 | 11.5 | 180° C., 2 hr | 24 | 5.47 |

TABLE 2

|  | Film thickness [nm] | Current density [mA/cm$^2$] | Voltage [V] | Brightness [cd/m$^2$] | Current efficiency [cd/A] | Light-emission initiating voltage [V] | Maximum brightness [cd/m$^2$] |
| --- | --- | --- | --- | --- | --- | --- | --- |
| Example 5 | 18 | 45.7 | 7.0 | 2365 | 5.17 | 2.75 | 35100 |
| Example 6 | 18 | 71.4 | 7.0 | 3804 | 5.33 | 2.75 | 28080 |

TABLE 2-continued

|  | Film thickness [nm] | Current density [mA/cm$^2$] | Voltage [V] | Brightness [cd/m$^2$] | Current efficiency [cd/A] | Light-emission initiating voltage [V] | Maximum brightness [cd/m$^2$] |
|---|---|---|---|---|---|---|---|
| Comparative Example 1 | — | 10 | 9.2 | 330 | 3.3 | 4.50 | 10640 |
| Comparative Example 1 | — | 0.37 | 7.0 | 1.2 | 0.32 | 4.50 | 10640 |
| Comparative Example 2 | 24 | 0.419 | 7.0 | 8.89 | 2.12 | 4.00 | 5540 |
| Comparative Example 2 | 12 | 10 | 10.2 | 239 | 2.39 | 6.50 | 4410 |
| Comparative Example 3 | 21 | 10 | 8.1 | 410 | 4.1 | 2.75 | 18799 |
| Comparative Example 3 | 21 | 2.86 | 7.0 | 101 | 3.5 | 2.75 | 18799 |

As shown in Table 2, it is appreciated that the OLED devices (Examples 5 and 6), which were provided with the hole-transporting thin films formed from the varnishes obtained in Examples 3 and 4, respectively, were lower in drive voltage and higher in current efficiency and maximum brightness than the OLED devices provided with no hole-transporting thin film. It is also appreciated that the OLED devices of Examples 5 and 6 were higher in current efficiency and maximum brightness than the devices of Comparative Example 3 in which as a dopant, 5-SSA was used instead of any arylsulfonic acid compound specified in the present invention. Further, the light-emitting surfaces of the OLED devices fabricated in Examples 5 and 6 were highly uniform, and no dark spots were observed there.

The invention claimed is:

1. An arylsulfonic acid compound represented by the following formula (1):

[Chemical Formula 1]

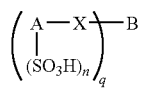

(1)

wherein,

X represents O or S,

A represents a naphthalene or anthracene ring which may contain one or more substituents other than X and (SO$_3$H)n, B represents an unsubstituted or substituted hydrocarbon group, a 1,3,5-triazine group, or an unsubstituted or substituted group represented by the following formula (3) or (4);

[Chemical Formula 2]

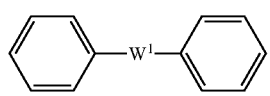

(3)

-continued

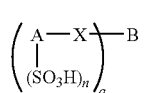

(4)

wherein W$^1$ and W$^2$ each independently represents O, S, an S(O) group, an S(O$_2$) group, or an unsubstituted or substituted N, Si, P or P(O) group, n indicates a number of sulfonic acid group(s) bonded to A, and stands for an integer satisfying 1≦n≦4, q indicates a number of B—X bond(s), and stands for an integer satisfying 2≦q.

2. The arylsulfonic acid compound according to claim 1, wherein B is a divalent or trivalent, substituted or unsubstituted benzyl group, a divalent, substituted or unsubstituted p-xylylene group, a divalent or trivalent, substituted or unsubstituted naphthyl group, a divalent or trivalent 1,3,5-triazine group, a divalent, substituted or unsubstituted diphenylsulfone group, a di- to tetra-valent, perfluorobiphenyl group, a divalent, substituted or unsubstituted 2,2-bis((hydroxypropoxy)phenyl)propyl group, or a substituted or unsubstituted polyvinylbenzyl group.

3. An electron-acceptor material comprising an arylsulfonic acid compound according to claim 1 or 2.

4. A charge-transporting varnish comprising an electron-acceptor material, a charge-transporting material, and a solvent;

wherein said electron-acceptor material comprises an arylsulfonic acid compound represented by the following formula (1) or (2):

[Chemical Formula 1]

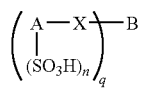

(1)

wherein,

X represents O, S or NH,

A represents a naphthalene or anthracene ring which may contain one or more substituents other than X and (SO$_3$H)n, B represents an unsubstituted or substituted hydrocarbon group, a 1,3,5-triazine group, or an unsubstituted or substituted group represented by the following formula (3) or (4);

[Chemical Formula 2]

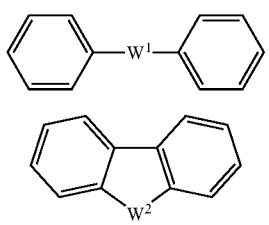

(3)

(4)

wherein $W^1$ and $W^2$ each independently represents O, S, an S(O) group, an S(O$_2$) group, or an unsubstituted or substituted N, Si, P or P(O) group, n indicates a number of sulfonic acid group(s) bonded to A, and stands for an integer satisfying $1 \leq n \leq 4$, q indicates a number of B—X bond(s), and stands for an integer satisfying $1 \leq q$.

5. The charge-transporting varnish according to claim 4, wherein B is a divalent or trivalent, substituted or unsubstituted benzyl group, a divalent, substituted or unsubstituted p-xylylene group, a divalent or trivalent, substituted or unsubstituted naphthyl group, a divalent or trivalent 1,3,5-triazine group, a divalent, substituted or unsubstituted diphenylsulfone group, a di- to tetra-valent, perfluorobiphenyl group, a divalent, substituted or unsubstituted 2,2-bis((hydroxypropoxy)phenyl)propyl group, or a substituted or unsubstituted polyvinylbenzyl group.

6. A charge-transporting thin film comprising an electron-acceptor material and an charge-transporting material; wherein said electron-acceptor material comprises an arylsulfonic acid compound represented by the following formula (1):

[Chemical Formula 1]

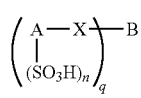

(1)

wherein,

X represents O, S or NH,

A represents a naphthalene or anthracene ring which may contain one or more substituents other than X and (SO$_3$H)n, B represents an unsubstituted or substituted hydrocarbon group, a 1,3,5-triazine group, or an unsubstituted or substituted group represented by the following formula (3) or (4);

[Chemical Formula 2]

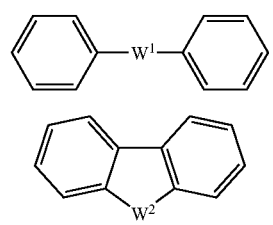

(3)

(4)

wherein $W^1$ and $W^2$ each independently represents O, S, an S(O) group, an S(O$_2$) group, or an unsubstituted or substituted N, Si, P or P(O) group, n indicates a number of sulfonic acid group(s) bonded to A, and stands for an integer satisfying $1 \leq n \leq 4$, q indicates a number of B—X bond(s), and stands for an integer satisfying $1 \leq q$.

7. An organic electroluminescent device comprising an charge-transporting thin film according to claim 6.

8. The charge-transporting thin film according to claim 6, wherein B is a divalent or trivalent, substituted or unsubstituted benzyl group, a divalent, substituted or unsubstituted p-xylylene group, a divalent or trivalent, substituted or unsubstituted naphthyl group, a divalent or trivalent 1,3,5-triazine group, a divalent, substituted or unsubstituted diphenylsulfone group, a di- to tetra-valent, perfluorobiphenyl group, a divalent, substituted or unsubstituted 2,2-bis((hydroxypropoxy)phenyl)propyl group, or a substituted or unsubstituted polyvinylbenzyl group.

9. An organic electroluminescent device comprising a charge-transporting thin film according to claim 8.

* * * * *